United States Patent
Pfeiffer et al.

(10) Patent No.: US 9,176,173 B2
(45) Date of Patent: Nov. 3, 2015

(54) METHOD FOR DETECTING IMPERFECT MOUNTING OF A ROD-SHAPED METALLIC OBJECT IN A METALLIC HOLLOW SHAFT AND A DEVICE

(75) Inventors: Wolfgang Pfeiffer, Freising (DE); Thomas Klein, Freising (DE)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 369 days.

(21) Appl. No.: 13/354,508

(22) Filed: Jan. 20, 2012

(65) Prior Publication Data

US 2013/0134997 A1 May 30, 2013

Related U.S. Application Data

(60) Provisional application No. 61/564,173, filed on Nov. 28, 2011.

(51) Int. Cl.
*G01R 27/08* (2006.01)
*H01L 21/00* (2006.01)
*G01M 13/00* (2006.01)
*G01N 1/00* (2006.01)

(52) U.S. Cl.
CPC ............ *G01R 27/08* (2013.01); *G01M 13/00* (2013.01); *H01L 21/00* (2013.01); *G01N 1/00* (2013.01); *H01L 2221/00* (2013.01)

(58) Field of Classification Search
CPC ...... H01L 21/00; H01L 2221/00; G01N 1/00; G01N 2201/00; B08B 1/00; B08B 2200/00; B01L 1/00; B01L 2200/00; B24B 1/00; B24B 5/00; B24B 29/00; B24B 41/00; B24B 49/00

USPC ......... 324/691, 693, 695, 699, 701, 718, 722, 324/421, 456, 207.26, 513, 525, 750.16, 324/750.22, 750.24, 750.25, 754.13, 545, 324/558, 76.74, 90, 143, 154 R, 157
See application file for complete search history.

(56) References Cited

U.S. PATENT DOCUMENTS

| | | | | |
|---|---|---|---|---|
| 4,272,776 A | * | 6/1981 | Weijland et al. | 257/511 |
| 5,448,442 A | * | 9/1995 | Farag | 361/24 |
| 5,473,254 A | * | 12/1995 | Asar | 324/537 |
| 6,115,867 A | * | 9/2000 | Nakashima et al. | 15/77 |
| 6,572,444 B1 | * | 6/2003 | Ball et al. | 451/10 |
| 6,766,813 B1 | * | 7/2004 | Sayka et al. | 134/148 |
| 6,967,586 B2 | * | 11/2005 | Narita et al. | 340/682 |
| 7,074,109 B1 | * | 7/2006 | Bennett et al. | 451/5 |
| 7,394,266 B2 | * | 7/2008 | Zaerpoor | 324/754.13 |
| 7,552,799 B2 | * | 6/2009 | Sherrington | 184/7.4 |
| 2001/0010103 A1 | * | 8/2001 | Konishi et al. | 15/77 |
| 2002/0017365 A1 | * | 2/2002 | Gunji et al. | 156/345 |
| 2002/0145421 A1 | * | 10/2002 | Rose | 324/207.26 |
| 2012/0049871 A1 | * | 3/2012 | Raj | 324/722 |

\* cited by examiner

*Primary Examiner* — Huy Q Phan
*Assistant Examiner* — Temilade Rhodes-Vivour
(74) *Attorney, Agent, or Firm* — Jacqueline J. Garner; Frank D. Cimino

(57) ABSTRACT

A method for detecting an imperfect mounting of an essentially rod-shaped metallic object in a metallic hollow shaft is provided. The imperfect mounting may lead to the formation of metallic particles. The rod-shaped object is mounted electrically insulated from the hollow shaft. The electrical resistance between the rod-shaped object and the hollow shaft is measured. An alert is issued when the electrical resistance is lower than a predefined level. A device includes a spin unit with a hollow drive shaft and a nozzle mounted inside the hollow shaft. The device is configured to use the inventive method.

6 Claims, 1 Drawing Sheet

METHOD FOR DETECTING IMPERFECT MOUNTING OF A ROD-SHAPED METALLIC OBJECT IN A METALLIC HOLLOW SHAFT AND A DEVICE

FIELD OF THE INVENTION

The invention relates to a method for detecting an imperfect mounting of a essentially rod-shaped metallic object in a metallic hollow shaft which may lead to the formation of metallic particles. The invention further relates to a device comprising a spin unit configured to use the method.

BACKGROUND

Some devices comprise a hollow drive shaft through which a rod-shaped object is passed. While the drive shaft is rotating the rod-shaped object remains fix.

An example for a device in which this kind of arrangement is used is a spin unit in wafer production. More specifically, a cleaning unit in wafer production comprises an electrical motor, a so-called spin motor, comprising a hollow shaft. The motor shaft may rotate with a velocity of about 1000 to 5000 rounds per minute (rpm). A common velocity is about 3000 rpm. The shaft of the spin motor is attached to a wafer holder for turning or spinning a wafer quickly.

Inside the hollow shaft a rinsing nozzle is mounted. Through the rinsing nozzle de-ionized water (DIW) is led to the wafer for high pressure rinsing or cleaning.

The nozzle is mounted to be stationary while the shaft turns round.

The drive shaft as well as the rinse nozzle is made of metal. The nozzle is mounted so that it is spaced from the inside wall of the drive shaft.

In practice, the metal nozzle must be remounted into the shaft after repair, preventive maintenance or still other occasions.

If due to an imperfect mounting the nozzle contacts the inside wall of the drive shaft this is not visible because it is inside the shaft. A slight contact will not hinder movement of the drive shaft either. However, grinding of the nozzle against the drive shaft leads to an abrasion of metal particles. These metal particles which may be very small are transported to the wafer surface due to the under-pressure in the cup in which the wafer is mounted.

As a result, short circuits occur on the circuits realized on the wafer due to the metallic particles. As entire wafers are concerned the influence on the production is important, the scrap rate increases severely. Furthermore, it is very difficult to locate the error source.

SUMMARY

It is an object of the invention to provide a method for detecting an imperfect mounting of an essentially rod-shaped metallic object in a metallic hollow shaft which may lead to the formation of metallic particles.

It is a further object of the invention to provide a device configured to use the method.

In one aspect of the invention a method is provided comprising as first step mounting the rod-shaped object electrically insulated from the hollow shaft. Normally, the chassis of an electrical motor and the drive shaft of the motor are connected to ground to prevent any electrical risks to humans in case of a malfunction of the electrical motor. The rod-shaped object passing through the hollow drive shaft is attached to a non-moving part of the motor. For applying the method provided by the invention the rod-shaped metallic object is to be electrically insulated from the drive shaft, this means also that the rod-shaped metallic object is not connected to ground. This can easily be achieved by any insulating material put between the rod-shaped object and the motor at the point of attachment.

In a next step, the electrical resistance between the rod-shaped object and the hollow shaft is measured. Measuring an electrical resistance is known in the prior art. In common Ohm meters a known voltage is applied to the two sides of an electrical resistance to be measured and the current flowing is measured. The electrical resistance can then be calculated. As the rod-shaped object is mounted electrically insulated from the hollow shaft the electrical resistance should be very high. If the rod-shaped metallic object is mounted so as to contact somewhere the inside of the metallic hollow shaft the measurement shows a much smaller electrical resistance.

In a next step, an alert is issued when the electrical resistance is lower than a predefined level. In a very simple realization the alert may be given for example by an LED. A buzzer to issue an acoustic alert could be used as well. It is possible to measure the resistance only once after mounting the rod-shaped object.

In a preferred embodiment, the electrical resistance is measured continually. Continually includes measuring continuously, i.e. without any interruptions as well as repetitive measurements separated by short time intervals for example every second, every minute and so on. A continuous measurement allows detecting a degradation which occurs only after a certain time, for example because the rod-shaped object was not fixed correctly and changes position due to vibrations or because the position changes with temperature or due to mechanical tensions.

In an embodiment, the hollow shaft is the drive shaft of a motor in a spin unit used in wafer production and the essentially rod-shaped metallic object is a nozzle. While metallic particles can be a nuisance in any application degrading the rod-shaped object and hindering rotation of the shaft at the long, metallic particles in a wafer production represent a real catastrophe. Wafer production is effectuated under clean-room conditions. Any particles are disturbing. Metallic particles on a wafer surface lead immediately to short circuits and destruction of the integrated circuit realized on the wafer. Furthermore, metallic particles coming from abrasion in a cleaning unit are not easily recognizable as error source.

In a preferred embodiment, the method further comprises a step of blocking start of the motor when there is an alert. As the importance of the error may not be recognizable at once to the user of the cleaning unit, start of the motor is blocked so that the cleaning unit cannot be used anymore when a contact is detected.

The invention further provides a device comprising a spin unit with a hollow drive shaft and a nozzle mounted inside the hollow shaft which is configured to use the method.

In an embodiment, the device comprises an insulator electrically insulating the nozzle from the hollow drive shaft. State-of-the-art insulators may be used. The device further comprises a measurement unit for measuring the electrical resistance between the nozzle and the hollow shaft. The measurement unit may be integrated to the spin unit or it may be provided as separate unit.

In an embodiment, an alert unit is provided configured to output an alert when the value of the electrical resistance drops under a given level. The user must not judge any values but is given the decision not to use the device any more.

In a preferred embodiment, the device comprises a control unit and the alert unit is configured to output the alert as an electrical signal to the control unit. The control unit is configured to block starting of the motor when there is an alert. The problem detected is so important that the device must not be used any more. By blocking start of the motor, the user or operator is hindered to continue utilization of the device.

The device may be part of a wafer production system and the alert is output to a system interface. This allows integrating the method into a whole system control signaling the problem to the system administrator, allowing for logging the alert etc.

In a further embodiment, the nozzle is provided with an electrical connection and the measurement unit is connected with one side to the electrical connection and with the other side to the electrical potential of the hollow shaft. As explained above, the hollow shaft is grounded so that no additional electrical contact or electrical connection is needed.

BRIEF DESCRIPTION OF DRAWINGS

Further aspects and characteristics of the invention ensue from the following description of the preferred embodiments of the invention with reference to the accompanying drawings, wherein.

DETAILED DESCRIPTION OF AN EXAMPLE EMBODIMENT

Figure 1:
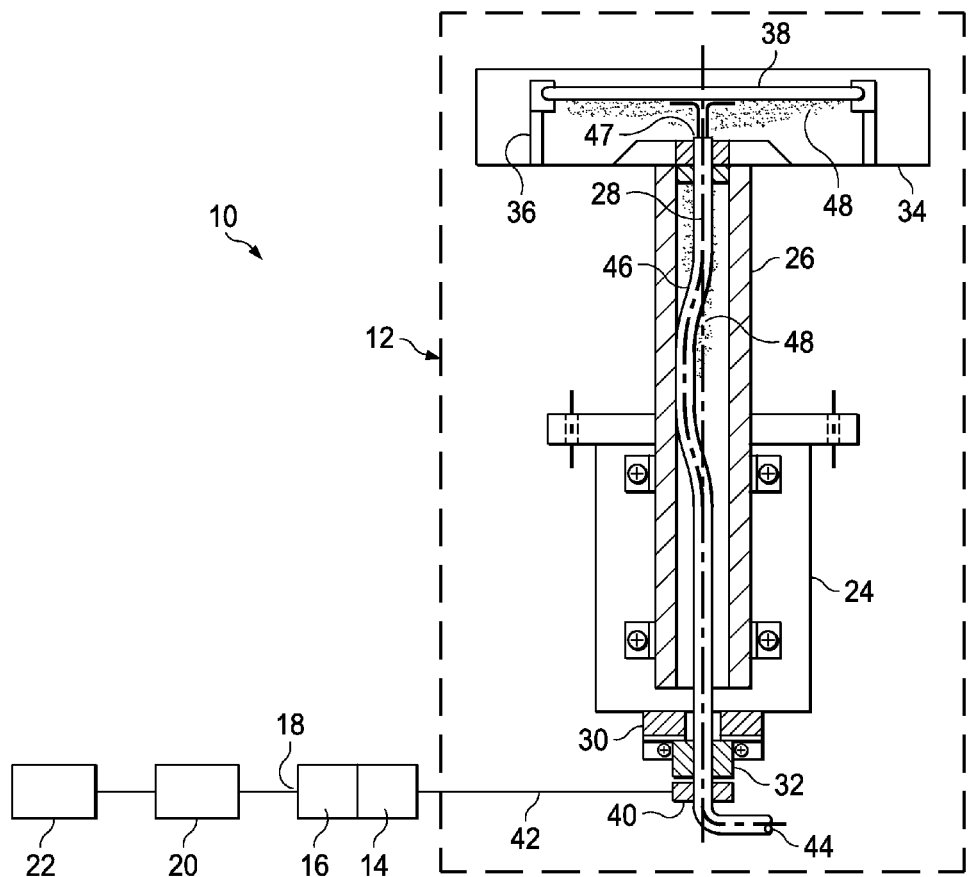
FIG. 1 is a schematic representation of a device according to the invention showing only components relevant for understanding the invention.

FIG. 1 shows schematically a device 10 comprising a spin unit 12, a measurement unit 14 and an alert unit 16. Alert unit 16 comprises an output 18 coupled to an interface 20. Interface 20 is coupled to a control unit 22 which may be implemented in a data processing unit as a server or host etc.

In the embodiment shown, spin unit 12 is a cleaning unit. A motor 24 is shown schematically. Motor 24 may be any electrical motor suitable to spin a wafer round with about 3000 rpm.

The schematically shown motor 24 comprises a hollow shaft 26 which is represented in a sectional view.

A wafer holder 36 is attached to motor shaft 26 so that the wafer holder turns with the motor shaft. A wafer 38 is held by wafer holder 36 turning together with the wafer holder and the motor shaft. A so-called cup 34 surrounds the wafer holder and wafer.

A rinse nozzle 28 passes through the hollow shaft 26. The rinse nozzle 28 is essentially a straight metallic tube. Rinse nozzle 28 is shown imperfectly mounted, this means that rinse nozzle 28 is mounted in a way which bends rinse nozzle 28. At a surface 46 rinse nozzle 28 contacts an inner wall of hollow shaft 28.

The rinse nozzle 28 is firmly attached to a part 30 of the motor chassis. An insulator 32 electrically insulates the rinse nozzle 28 from motor 24. This implies that rinse nozzle 28 is also electrically insulated from motor shaft 26.

An electrical connection 40 is provided to rinse nozzle 28. The electrical connection 40 is connected by a cable 42 to an input of measurement unit 14.

Rinse nozzle 28 is hollow. Rinse nozzle 28 is connected at an end 44 to a de-ionized water supply. The de-ionized water is sent under pressure through rinse nozzle 28 to an end 47 of rinse nozzle 28. The de-ionized water is thus directed onto the surface of wafer 38 intended to clean the wafer surface.

In operation, motor 24 which is also called a spin motor is operating and motor drive shaft 28 rotates along a rotation axis A with a speed of about 3000 rpm. This is an often used speed but other speeds as 2000 or 4000 rpm are possible as well as any speeds in between.

As cup 34 is attached to a face of motor shaft 28 it turns with the same speed as shaft 28. Together with cup 34 wafer holder 36 and wafer 38 spin around. De-ionized water impinges on the center of wafer 38 and with the rapid rotation of the wafer the DIW is cleaning the whole wafer surface.

As shaft 28 rotates around axis A and rinse nozzle 28 remains stationary, abrasion of metal particles 48 occurs at the contact surface 46. As cup 34 is under-pressurized, the metal particles 48 are drawn into cup 34 and metal particles 48 are deposited on the wafer surface. They degrade severely the wafer.

The measurement unit 14 is electrically connected to the electrical connection 40 and thereby to rinse nozzle 28. A second not shown measurement point of measurement unit 14 is connected to ground. Motor 24 together with motor shaft 26 and motor fixing part 30 are grounded as well. Measurement unit 14 may be a state-of-the-art Ohm meter.

Measurement unit 14 measures a small resistance because the metallic rinse nozzle 28 contacts the metallic motor shaft 26. If the measured resistance value is under a predefined level, alert unit 16 outputs an electrical signal at output 18. The predefined level is set so that in case the contact is thus that metal abrasion occurs, the electrical resistance measured lies under the level. The electrical signal is input to interface 20 and transmitted to control unit 22.

Control unit 22 is configured to be able to block restart of the motor. Next time the wafer is changed, this means next time a new wafer is put into the cleaning unit for being rinsed with de-ionized water, motor 24 is blocked and cannot be started anymore. The control unit 22 may further generate a message to the system operator according to which cleaning unit 12 has the rinse nozzle 28 mounted in a way contacting hollow shaft 26.

Figure 2:
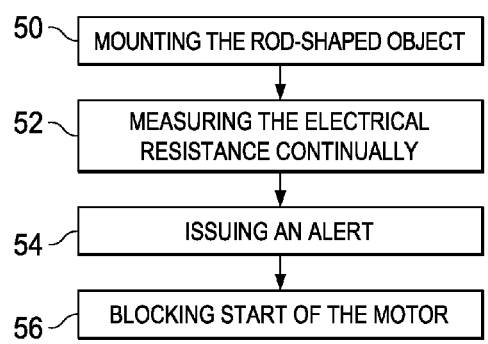
FIG. 2 shows a flow diagram illustrating the steps according to the inventive method.

FIG. 2 illustrates the steps according to the inventive method. In a first step 50 a rod-shaped object is mounted into a hollow shaft in a way that the rod-shaped object shall not contact the shaft. The shaft is configured to rotate while the rod-shaped object is configured to stay stationary. The rod-shaped object is mounted electrically insulated from the hollow shaft.

In an embodiment, the rod-shaped object is a rinsing nozzle of a cleaning unit used in the wafer production to clean the wafer surface. The hollow shaft is a motor shaft of an electrical motor rotating with about 3000 rpm. Once the rod-shaped object mounted it is not visible anymore. There is no possibility to visually control whether there is an unintentional contact between the rod-shaped object and the inner wall of the shaft.

In a next step 52, the electrical resistance between the rinse nozzle and the hollow shaft is measured, preferably continually. If the rod-shaped object is mounted correctly, there is no contact between nozzle and shaft and the electrical resistance is very high. When the electrical resistance measured falls beyond a predefined level this means that there is a contact between the rod-shaped object and the hollow shaft.

In a next step 54, an alert is issued if the electrical resistance measured is beyond a predefined level. The operator or user is informed that there is a contact between nozzle and shaft and a risk of metal abrasion.

In a preferred embodiment, this alert is sent in a step 56 to a control unit for blocking a restart of the motor. Each wafer remains only for a limited time in the cleaning unit, then the motor is stopped and the wafer is changed before the next cleaning cycle is started. Once an alert issued the motor does not start anymore, a new cleaning cycle cannot be started.

Although the invention has been described hereinabove with reference to specific embodiments, it is not limited to these embodiments and no doubt further alternatives will occur to the skilled person that lie within the scope of the invention as claimed.

The invention claimed is:

1. A method for cleaning a wafer, comprising the steps of:
inserting a nozzle through a hollow drive shaft;
placing an insulator structure between the nozzle and the hollow drive shaft such that the nozzle is electrically insulated from the hollow drive shaft;
placing a wafer in a wafer cup connected to the hollow drive shaft;
spinning the wafer by rotating the hollow drive shaft without rotating the nozzle;
directing a liquid through the nozzle and onto the wafer while spinning the wafer;
measuring the electrical resistance between the nozzle and the hollow drive shaft; and
issuing an alert when the electrical resistance is lower than a predefined level.

2. The method of claim 1, wherein the electrical resistance is measured continually.

3. The method according to claim 1, further comprising the step of blocking start of the motor if there is an alert.

4. A system for cleaning a wafer, comprising:
a hollow drive shaft;
a nozzle inserted through the hollow drive shaft;
an insulator structure between the nozzle and the hollow drive shaft such that the nozzle is electrically insulated from the hollow drive shaft;
a wafer cup connected to the hollow drive shaft such that the wafer cup and the hollow drive shaft are operable to be rotated without rotating the nozzle;
a motor connected to the hollow drive shaft, the motor and hollow drive shaft connected to ground;
a measurement unit connected to the nozzle and to ground to measure the electrical resistance between the nozzle and the hollow drive shaft and generate a signal when the electrical resistance is lower than a predefined level.

5. The system of claim 4, further comprising a control unit connected to through an interface to the measurement unit, the control unit operable to block operation of the motor in response to the signal.

6. The method of claim 1, wherein the insulator structure is placed between the nozzle and the hollow drive shaft such that the nozzle is electrically insulated from the hollow drive shaft prior to the step of spinning the wafer by rotating the hollow drive shaft without rotating the nozzle.

* * * * *